United States Patent

Zima et al.

Patent Number: 5,391,780
Date of Patent: Feb. 21, 1995

[54] AQUEOUS PROCESS FOR PREPARING AMIDO-CARBOXYLIC ACIDS BY REACTING AN AMINOACID WITH A CARBOXYLIC ACID ANHYDRIDE

[75] Inventors: George C. Zima, Kingsport; T. Hugh Williams, Fall Branch, both of Tenn.

[73] Assignee: Eastman Chemical Company, Kingsport, Tenn.

[21] Appl. No.: 228,613

[22] Filed: Apr. 15, 1994

[51] Int. Cl.$^6$ .................................. C07C 231/02
[52] U.S. Cl. ........................ 554/69; 554/63; 554/154; 554/161
[58] Field of Search ............... 554/69, 154, 161, 68, 554/63

[56] References Cited

U.S. PATENT DOCUMENTS

| | | | |
|---|---|---|---|
| 2,453,234 | 11/1948 | Keck | 260/534 |
| 2,956,068 | 10/1960 | Dohr et al. | 260/404.5 |
| 3,796,751 | 3/1974 | Fuhrmann et al. | 554/63 |

FOREIGN PATENT DOCUMENTS 648889 1/1951 United Kingdom.

*Primary Examiner*—José G. Dees
*Assistant Examiner*—Deborah D. Carr
*Attorney, Agent, or Firm*—John D. Thallemer; John F. Stevens

[57] ABSTRACT

This invention relates to a process for preparing amido-carboxylic acids in water. The process involves four steps. Step (A) involves hydrolyzing a lactam at a temperature of 150° C.–300° C. to form a mixture containing an amino acid. Step (B) involves cooling the reaction mixture formed in Step (A) to a temperature of 25° C.–100° C. Step (C) involves reacting a carboxylic acid anhydride with the amino acid formed in Step (A) to form a reaction mixture containing an organic layer which contains an amido-carboxylic acid and an aqueous layer. Step (D) involves separating the amido-carboxylic acid containing organic layer from the aqueous layer. The presence of water aids in product isolation by phase separation and recycle of the reactants. Amido-carboxylic acids are used to make bleach activators for detergents.

10 Claims, No Drawings

AQUEOUS PROCESS FOR PREPARING AMIDO-CARBOXYLIC ACIDS BY REACTING AN AMINOACID WITH A CARBOXYLIC ACID ANHYDRIDE

FIELD OF INVENTION

This invention relates to a process for preparing amido-carboxylic acids in water. The process involves four steps. Step (A) involves hydrolyzing a lactam at a temperature of 150° C.–300° C. to form a mixture containing an amino acid. Step (B) involves cooling the reaction mixture formed in Step (A) to a temperature of 25° C.–100° C. Step (C) involves reacting a carboxylic acid anhydride with the amino acid formed in Step (A) to form a reaction mixture containing an organic layer which contains an amido-carboxylic acid and an aqueous layer. Step (D) involves separating the amido-carboxylic acid containing organic layer from the aqueous layer. The presence of water aids in product isolation by phase separation and recycle of the reactants. Amido-carboxylic acids are used to make bleach activators for detergents.

BACKGROUND OF THE INVENTION

Amido-carboxylic acids are industrial chemical intermediates for the preparation of many chemicals used in commerce. Amido-carboxylic acids are prepared by reacting a lactam with a carboxylic acid. Amido-carboxylic acids are also prepared by reacting a carboxylic acid, carboxylic acid chloride, carboxylic acid anhydride or carboxylic acid ester with an amino carboxylic acid which is prepared by hydrolysis of a lactam. These processes to form amido-carboxylic acids are referred to as amidation reactions.

It is known to convert lactams by hydrolysis into the corresponding amino-carboxylic acids in the presence of hydrolysis promoting reagents such as hydrochloric acid. However, pure amino-acids are not directly obtained. In the case where hydrochloric acid is used as the promoting reagent, the amino-acid-hydrochloride is obtained and the separation of the free carboxylic acid is cumbersome and expensive.

U.S. Pat. No. 2,453,234 discloses a process for preparing an amino-carboxylic acid by hydrolyzing a lactam by means of at least 10 moles of water per mole of lactam to produce an amino-carboxylic acid. Great Britain Pat. No. 648,889 discloses a process for preparing amino-carboxylic acids by heating aliphatic or cyclo-aliphatic lactams in the presence of more than 20 moles of water per mole of lactam. U.S. Pat. No. 2,956,068 discloses a process for preparing amido-carboxylic acids by reacting a lactam with a free carboxylic acid in the presence of catalytic amounts of water. The reaction product is obtained as a solid crystal mass which is subsequently suspended in water and neutralized.

In contrast, the present inventors have unexpectedly discovered a process for preparing amido-carboxylic acids from a lactam and a carboxylic acid anhydride in water. It is unexpected that an amido-carboxylic acid could form by the reaction of a carboxylic acid anhydride with an amino acid in the presence of water. Moreover, it is unexpected that in the reaction of amino acids with carboxylic acid anhydrides, the lactam precursor of the amino acids does not react with the carboxylic anhydride. The amido-carboxylic acids obtained by this process essentially contain one molecule of amino acid and one molecule of carboxylic acid, and are essentially free of undesirable byproducts.

SUMMARY OF THE INVENTION

Accordingly, it is one object of the present invention to provide a process for preparing amido-carboxylic acids.

Accordingly, it is another object of the invention to provide a process for preparing amido-carboxylic acids in water.

These and other objects are accomplished herein by a process for preparing amido-carboxylic acids in water, said process comprising the steps of:

(A) reacting at a temperature of 150° C.–300° C. for 2 to 10 hours, a mixture containing
  (1) a lactam containing at least 3 carbon atoms per molecule; and
  (2) 10 to 50 moles of water per mole of the lactam to form a mixture containing an amino acid;

(B) cooling the reaction mixture formed in Step (A) to a temperature of 25° C.–100° C.;

(C) reacting at a temperature of 25° C.–100° C. for 5 minutes to 1 hour
  (3) 1 to 10 moles of a carboxylic acid anhydride having 6 to 26 carbon atoms with the amino acid formed in Step (A) to form a reaction mixture containing an organic layer which contains an amido-carboxylic acid and an aqueous layer; and (D) separating the amido-carboxylic acid containing organic layer from the aqueous layer.

DESCRIPTION OF THE INVENTION

The process of the present invention involves four steps. In the first step, Step (A), water and a lactam are combined in a reactor at a temperature of 150° C.–300° C. for 2 to 10 hours. The reactor must be able to be heated and must contain the pressure of the reaction. Preferably, the reactor is an autoclave. The reaction in Step (A), involves hydrolysis of the lactam forming an amino acid.

The lactam, component (1), contains at least 3 carbon atoms per molecule. Suitable lactam monomers contain at least 3 carbon atoms per molecule, preferably 4 to 7 carbon atoms per molecule. Suitable lactam monomers include butyrolactam, valerolactam, epsilon-caprolactam, beta-propiolactam, delta-valerolactam, and similar lactams. These lactams may be substituted at the nitrogen atom by lower hydrocarbon radicals containing for example, 1–3 carbon atoms. For example, methylcaprolactam may be used. Epsilon-caprolactam and substituted derivatives thereof are the preferred lactam monomers.

Component (2) is water which includes tap water and distilled water. Distilled water is preferred since tap water may contain metal salts which in combination with the carboxylic acid anhydride could form surface active agents and inhibit isolation of the product. Water is present in an amount of 10 to 50 moles, preferably, 20 to 40 moles per mole of the lactam. Most preferably, the water is present in an amount of 30 to 35 moles per mole of the lactam. Insufficient water results in insufficient hydrolysis of the lactam to the amino acid. Although there is no critical higher limit to the amount of water, the use of greater than 50 mole percent water creates a situation where it is increasingly difficult to separate the small organic phase from the aqueous phase and would render the process unnecessarily expensive from the point of view of recovering the desired product in pure form.

The reaction of Step (A) may be carried out over a wide range of temperatures, but at temperatures below 150° C. the reaction rate of hydrolysis of the lactam monomer is very slow. On the other hand, it is generally not desirable to exceed temperatures above 300° C. inasmuch as polymerization of the lactam may take place. In addition, at such high temperatures, a higher operating pressure would be needed to contain the water. Accordingly, a temperature between 150°–300° C. is satisfactory. Temperatures of 200° to 250° C. are particularly desirable in the substantial absence of oxygen. The time of the reaction is generally 2 to 10 hours, preferably 4 to 8 hours.

The reaction product of Step (A) is an amino acid which has the general formula $NH_2(CRR')_nCOOH$ and is characterized by a basic amino group ($NH_2$) and an acidic carboxyl group (COOH). The letter n in the formula is 1–26, preferably 1–10. The R and R' groups are independently selected from hydrogen, unsubstituted or substituted straight chain or branched $C_1$–$C_{20}$ alkyl, unsubstituted or substituted $C_3$–$C_8$ cycloalkyl, $C_3$–$C_8$ alkenyl, $C_3$–$C_8$ alkynyl, and $C_6$–$C_{14}$ aryl.

The unsubstituted and substituted $C_3$–$C_8$ cycloalkyl groups mentioned above refer to cycloaliphatic hydrocarbon groups which contain 3 to 8 carbons in the ring, preferably 5 or 6 carbons, and these cycloalkyl groups substituted with one or two of $C_1$–$C_4$ alkyl, $C_1$–$C_4$ alkoxy, hydroxy or $C_1$–$C_4$ alkanoyloxy.

The $C_3$–$C_8$ alkenyl and $C_3$–$C_8$ alkynyl groups represent straight or branched chain hydrocarbon radicals containing 3 to 8 carbons in the chain and which contain a carbon-carbon double bond or a carbon—carbon triple bond, respectively.

The term "aryl" is used to include carbocyclic aryl groups containing up to fourteen carbons, e.g., phenyl and naphthyl, and those substituted with one or two groups selected from $C_1$–$C_4$-alkyl, $C_1$–$C_4$ alkoxy, $C_1$–$C_4$-alkoxycarbonyl, $C_1$–$C_4$-alkanoyloxy, $C_1$–$C_4$-alkanoylamino, halogen, cyano, $C_1$–$C_4$-alkylsulfonyl, $C_1$–$C_4$-alkylene-$(OH)_n$, O—$C_1$–$C_4$-alkylene-$(OH)_n$, —S—$C_1$–$C_4$-alkylene-$(OH)_n$, —$S_2$—$C_1$–$C_4$-alkylene-$(OH)_n$, —$CO_2$—$C_1$–$C_4$-alkylene-$(OH)_n$, —$SO_2N(R_{17})$-$C_1$–$C_4$-alkylene —$(OH)_n$, —$SO_2N(C_1$–$C_4$-alkylene —$(OH)_2$, —$CON(R_{17})C_1$–$C_4$-alkylene-$(OH)_n$, —CON(-$C_1$–$C_4$-alkylene-$(OH)_2$, —$N(SO_2C_1$–$C_4$-alkyl)-alkylene-$(OH)_n$ or —$N(SO_2$ phenyl)-$C_1$–$C_4$-alkylene-$(OH)_n$; wherein n is one or two.

The term "aryl" is also used to include heterocyclic aryl groups such as a 5 or 6-membered heterocyclic aromatic ring containing one oxygen atom, and/or one sulfur atom, and/or up to three nitrogen atoms, said heterocyclic aryl ring optionally fused to one or two phenyl rings or another 5 or 6-membered heteroaryl ring. Examples of such ring systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl, and the like and those rings substituted with one or more substituents listed above in the definition of the term "aryl".

In addition, the term "aryl" includes arylene groups. The term "arylene" is used to represent a divalent carbocyclic aryl hydrocarbon moiety containing up to fourteen carbons, e.g., o-, m- and p-phenylene, and those substituted with one or two groups selected from $C_1$–$C_4$-alkyl, $C_1$–$C_4$-alkoxy or halogen.

In the second step, Step (B), the reaction mixture formed in Step (A) is cooled to a temperature of 25° C.–100° C. Step (B) may be conducted in the same vessel as Step (A) in a batch process, or Step (B) may be conducted in a separate vessel using either a batch process or a continuous process. Cooling is accomplished by methods known in the art such as external cooling with water, ice or through the use a cooling jacket.

In the third step, Step (C), a carboxylic acid anhydride, component (3), is reacted with the amino acid formed in Step (A) to form a reaction mixture containing an organic layer which contains an amido-carboxylic acid and an aqueous layer. Component (3) is a carboxylic acid anhydride having 6–26 carbon atoms, preferably 8–20 carbon atoms, and most preferably 8–10 carbon atoms. The carboxylic acid anhydride may contain more than one carboxylic acid group. Examples of carboxylic acid anhydrides are: caprylic anhydride, pelargonic anhydride, capric anhydride, undecylic anhydride, lauric anhydride, palmitic anhydride, stearic anhydride, oleic anhydride, linoleic anhydride, behenic anhydride, terephthalic anhydride, phthalic anhydride, isophthalic anhydride, naphthalene-2,6-dicarboxylic anhydride, cyclohexanedicarboxylic anhydride, cyclohexanediacetic anhydride, diphenyl-4,4'-dicarboxylic anhydride, succinic anhydride, glutaric anhydride, adipic anhydride, azelaic anhydride, sebacic anhydride, and the like. Preferred carboxylic anhydrides are capric anhydride and caprylic anhydride.

The carboxylic acid anhydride is present in an amount of 1 to 10 moles, preferably, 1 to 5 moles per mole of lactam. Most preferably, the carboxylic acid anhydride is present in an amount of 1 to 2 moles per mole of lactam. Insufficient carboxylic acid anhydride results in incomplete reaction with the amino acid. Although there is no critical higher limit to the amount of carboxylic acid anhydride, in practice one will not use a higher ratio than is strictly necessary to react with all of the amino acid present since to do so would render the process unnecessarily expensive from the point of view of consuming carboxylic acid anhydride to form carboxylic acid by hydrolysis instead of the desired product. Most preferably, the molar ratio for the water, carboxylic acid anhydride, and lactam is 33:1.5:1, respectively.

The reaction of Step (C) may be carried out over a wide range of temperatures, but at temperatures below 25° C. the reaction rate of the amino acid with the carboxylic acid anhydride is slow. On the other hand, it is generally not desirable to exceed temperatures above 100° C. because a higher operating pressure would be needed to contain the water from the reaction medium. Accordingly, a temperature between 60°–80° C. is particularly desirable in the substantial absence of oxygen. It is important to note, however, that the reaction must be conducted at a temperature above the melting point of the carboxylic acid anhydride. The time of the reaction is generally 5 minutes to 1 hour, preferably 15 to 30 minutes.

The fourth step, Step (D), involves separation of the organic phase which contains carboxylic acids and the amido-carboxylic acid product from the aqueous phase which contains amino acids and water. Step (D) may be conducted in the same vessel as Steps (A)–(D) in a batch process, or Step (D) may be conducted in a separate vessel using either a batch process or a continuous process. Separation is accomplished by methods known in the art such as decantation. The carboxylic acids and unreacted lactam which remain in the organic phase are easily separated from the amido-carboxylic acid by distillation or crystallization and are recycled along with the aqueous phase.

Optionally, an acid catalyst may be added to the process to increase the speed of the reaction of the carboxylic acid anhydride with the amino acid. Suitable catalysts include carboxylic acids such as acetic acid or mineral acids such as sulfuric acid. Very small quantities of the catalyst are sufficient, such as from 0.001% to 1% based on the weight of the reactants in the reaction mixture.

The process of the present invention will be further illustrated by a consideration of the following examples, which are intended to be exemplary of the invention.

EXAMPLE 1

The following ingredients were combined in a 250 ml round-bottom flask equipped with a heating mantle, stirring bar, and thermometer: 200 grams of the hydrolysis product derived from the hydrolysis of 1443 grams of caprolactam, 7800 grams of water and 160 grams of acetic acid (equivalent to 10 grams (0.076 mole) 6-aminocaproic acid). The mixture was stirred and heated to 65° C. at which time 1.0 equivalent of decanoic anhydride was added to the flask. A two-phase system formed which emulsified upon stirring. The reaction was completed after 20 minutes and the reaction was cooled. Phase separation resulted when the stirring was stopped. The aqueous layer was separated from the organic layer.

The products in the organic layer were isolated by liquid—liquid phase separation. Unreacted caprolactam and 6-aminocaproic acid, a reaction intermediate, were retained primarily in the aqueous layer. The composition and amounts of compounds in the organic layer and in the aqueous layer are listed in Table I and Table II.

EXAMPLE 2

The decanoic anhydride from Example 1 was replaced with a mixture of octanoic/decanoic anhydride. The reaction conditions are set forth in Example 1.

TABLE I

| Organic Layer Composition For Example 1 | |
|---|---|
| Grams of Organic Layer | 47.8 g |
| Caprolactam | 6.6 g |
| Decanoic acid | 27.5 g |
| Amino caproic acid | 0.8 g |
| Acylcaprolactam | ND |
| Amido caproic acid | 11.0 g |
| Diamido caproic acid | 1.9 g |

*ND refers to none detected

Analysis of the organic phase indicated formation of decanamidocaproic acid and diamido acid with no detectable amount of undesirable byproduct acyl caprolactam which would have formed if caprolactam reacted with decanoic acid anhydride as expected. Most of the unreacted caprolactam and 6-aminocaproic acid were present in the aqueous phase and were recycled to the reactor.

TABLE II

| Aqueous Layer Composition For Example 1 | |
|---|---|
| Grams of Aqueous Layer | 171.2 g |
| Water | 153.6 g |
| Caprolactam | 12.2 g |
| Decanoic acid | ND |
| Amino caproic acid | 4.7 g |
| Acylcaprolactam | ND |
| Amidocaproic acid | ND |
| Diamidocaproic acid | ND |

*ND refers to none detected

Many variations will suggest themselves to those skilled in this art in light of the above detailed description. All such obvious modifications are within the full intended scope of the appended claims.

What is claimed is:

1. A process for preparing amido-carboxylic acids in water, said process comprising the steps of:
   (A) reacting at a temperature of 150° C.–300° C. for 2 to 10 hours, a mixture containing
      (1) a lactam containing at least 3 carbon atoms per molecule; and
      (2) 10 to 50 moles of water per mole of the lactam to form a mixture containing an amino acid;
   (B) cooling the reaction mixture formed in Step (A) to a temperature of 25° C.–100° C.;
   (C) reacting at a temperature of 25° C.–100° C. for 5 minutes to 1 hour
      (3) 1 to 10 moles of a carboxylic acid anhydride having 6 to 26 carbon atoms with the amino acid formed in Step (A) to form a reaction mixture containing an organic layer which contains an amido-carboxylic acid and an aqueous layer; and
   (D) separating the amido-carboxylic acid containing organic layer from the aqueous layer.

2. The process of claim 1 which additionally contains an acid catalyst.

3. The process of claim 2 wherein the acid catalyst is a carboxylic acid which is added in an amount of from 0.001 to 1 weight percent based on the weight of the reactants.

4. A process for preparing amido-carboxylic acids in water, said process comprising the steps of:
   (A) reacting at a temperature of 150° C.–300° C. for 2 to 10 hours, a mixture containing
      (1) a lactam containing 4 to 7 carbon atoms per molecule; and
      (2) 20 to 40 moles of water per mole of the lactam to form a mixture containing an amino acid;
   (B) cooling the reaction mixture formed in Step (A) to a temperature of 25° C.–100° C.;
   (C) reacting at a temperature of 25° C.–100° C. for 5 minutes to 1 hour
      (3) 1 to 5 moles of a carboxylic acid anhydride having 8 to 20 carbon atoms with the amino acid formed in Step (A) to form a reaction mixture containing an organic layer which contains an amido-carboxylic acid and an aqueous layer; and
   (D) separating the amido-carboxylic acid containing organic layer from the aqueous layer.

5. The process of claim 2 wherein the carboxylic acid anhydride, component (3), is selected from the group consisting of caprylic anhydride, pelargonic anhydride, capric anhydride, undecylic anhydride, lauric anhydride, palmitic anhydride, stearic anhydride, oleic anhydride, linoleic anhydride, behenic anhydride, terephthalic anhydride, phthalic anhydride, isophthalic anhydride, naphthalene-2,6-dicarboxylic anhydride, cyclohexanedicarboxylic anhydride, cyclohexanediacetic anhydride, diphenyl-4,4'-dicarboxylic anhydride, succinic anhydride, glutaric anhydride, adipic anhydride, azelaic anhydride, and sebacic anhydride.

6. The process of claim 4 wherein the carboxylic acid anhydride is selected from the group consisting of capric anhydride and caprylic anhydride.

7. A process for preparing amido-carboxylic acids in water, said process comprising the steps of:

(A) reacting at a temperature of 200° C.–250° C. for 4 to 8 hours, a mixture containing
  (1) a lactam selected from the group consisting of butyrolactam, valerolactam, epsilon-caprolactam, beta-propiolactam, delta-valerolactam, and similar lactams; and
  (2) 30 to 35 moles of water per mole of the lactam to form a mixture containing an amino acid;

(B) cooling the reaction mixture formed in Step (A) to a temperature of 60° C.–80° C.;

(C) reacting at a temperature of 60° C.–80° C. for 15 minutes to 30 minutes
  (3) 1 to 2 moles of a carboxylic acid anhydride having 8 to 10 carbon atoms with the amino acid formed in Step (A) to form a reaction mixture containing an organic layer which contains an amido-carboxylic acid and an aqueous layer; and (D) separating the amido-carboxylic acid containing organic layer from the aqueous layer by decantation.

8. The process of claim 3 wherein the lactam, component (1), is epsilon-caprolactam.

9. The process of claim 3 wherein the water, component (2), is distilled water.

10. The process of claim 3 wherein the molar ratio for the water, carboxylic acid anhydride, and lactam is 33:1.5:1, respectively.

* * * * *